United States Patent [19]

Kachel et al.

[11] 4,070,617

[45] Jan. 24, 1978

[54] DEVICE FOR CONTROLLING THE PARTICLE FLOW IN AN APPARATUS FOR MEASURING THE PROPERTIES OF PARTICLES SUSPENDED IN LIQUID

[75] Inventors: Volker Kachel, Gauting; Ewald Glossner, Munich, both of Germany

[73] Assignee: Max-Planck-Gesellschaft zur Forderung der Wissenschaften e.v., Gottingen, Germany

[21] Appl. No.: 711,224

[22] Filed: Aug. 3, 1976

Related U.S. Application Data

[63] Continuation of Ser. No. 533,657, Dec. 17, 1974, abandoned.

[30] Foreign Application Priority Data

May 8, 1974 Germany .............................. 2422119

[51] Int. Cl.² ........................................... G01N 27/07
[52] U.S. Cl. ............................................... 324/71 CP
[58] Field of Search .................. 324/71 CP; 356/102; 235/92 PC; 73/432 PS; 128/2 G

[56] References Cited

U.S. PATENT DOCUMENTS

| | | | |
|---|---|---|---|
| 3,299,354 | 1/1967 | Hogg ............................... | 324/71 CP |
| 3,340,471 | 9/1967 | Coulter, Jr. ..................... | 324/71 CP |
| 3,504,185 | 3/1970 | Zweig et al. ............. | 324/71 CP UX |
| 3,688,191 | 8/1972 | Claps .............................. | 324/71 CP |
| 3,793,587 | 2/1974 | Thom ............................. | 324/71 CP |

Primary Examiner—Gerard R. Strecker
Attorney, Agent, or Firm—Edwin E. Greigg

[57] ABSTRACT

An apparatus for investigating the properties of particles held in liquid suspension using the Coulter process, U.S. Pat. No. 2,656,508, wherein the flowrate of the particle suspension into the particle-free electrolyte carrier depends on the pressure difference between these two liquids. This pressure difference is made readily adjustable by setting the height of the level of the electrolyte by means of a separate, vertically movable chamber attached with a flexible lead to the main measuring chamber. The main measuring chamber is closed to the atmosphere, permitting maintenance of a pressure differential with respect to the atmosphere and with respect to the particle suspension.

22 Claims, 2 Drawing Figures

DEVICE FOR CONTROLLING THE PARTICLE FLOW IN AN APPARATUS FOR MEASURING THE PROPERTIES OF PARTICLES SUSPENDED IN LIQUID

This is a continuation of application Ser. No. 533,657, filed Dec. 17, 1974 now abandoned.

BACKGROUND OF THE INVENTION

The invention relates to an apparatus for the measurement of certain properties of particles held in a particle suspension, including a main measuring chamber divided into a first and a second chamber, wherein the first chamber includes a first electrode and is supplied with an electrolyte free from particles, which flows through a measurement aperture into the second chamber including a second electrode and within which the prevailing pressure is lower than the prevailing pressure in the first chamber, and where the particle suspension flows into the liquid stream ahead of the measuring opening whenever the pressure in the supply capillary tube which is disposed in the first chamber ahead of the measuring aperture is greater than the pressure prevailing in the first chamber.

Apparatus of this type is known (Spielmann/ Goren, Journal of Colloid and Interface Science 26, Pages 175-182 (1968); DAS No. 2 013 799). The mesurement described there is made according to the so-called "Coulter" Process (U.S. Pat. No. 2 656,508), which is based on the principle that, when a particle passes through the measuring aperture between the two electrodes, the different electrical properties of the particles on the one hand, and that of the electrolyte on the other hand, permit conclusions as to the properties of the particle which passed through the aperture (for example the volume) and, at the same time, when several particles pass the measuring aperture sequentially, the totality of all the pulses or signals which occur could be utilized, for example by classification, so as to obtain, for example, the volume distribution function. The known apparatus provides that the supply capillary dips into the first chamber, which is open to the atmosphere, ahead of the measuring aperture and that the particle suspension flows into the streaming electrolyte ahead of the measuring aperture due to the excess pressure prevailing in the supply capillary which is obtained in that the level of the particle suspension in the supply capillary is higher than the level of th electrolyte in the first chamber by an amount chosen so that the excess pressure in the supply capillary is sufficient to achieve the outward flow of the particle suspension in opposition to the flow resistances within the supply capillary tube.

By contrast to the apparatus described above, other devices (for example, those described in DAS No. 1 806 512, and in Thom: "Comparative investigations for electronic cell volume analysis", AEG-Telefunken, 1972, pages 16/17) which also operate on the above-mentioned "Coulter" process, but which provide that the outlet aperture of the supply capillary lies so close to the measuring aperture that, when the stream flows around the outlet aperture, the hydrodynamic suction, which may be calculated from Bernoulli's equation, is sufficient to draw the particle suspension out of the supply capillary without the necessity of providing excess pressure within the capillary relative to the static pressure in the chamber ahead of the measuring aperture.

A disadvantage of the known apparatus lies in that the outlet stream velocity of the particle suspension, i.e. the velocity with which it leaves the outlet aperture of the supply capillary, can be adjusted only with great difficulty and in a time-consuming manner, by changing the level of either the particle-free liquid or of the fluid in the suspension container. However, a simpler adjustment is desired, depending on the character of the particle suspension which must be examined, so as to account for different particle densities within the suspension, different particle sizes and different conditions of use of the data. For example, it may happen that a particular outlet velocity, which may be completely suitable for a particular particle suspension, would lead to an undesirable simultaneous passage of several particles with another particle suspension, or conversely, that the temporal separation between individual particles passing through the aperture becomes so large that an increase of the outlet velocity may be desirable for economic reasons.

OBJECT AND SUMMARY OF THE INVENTION

It is the principal object of the invention to provide an apparatus of the type described above in which the outlet flow velocity with which the particle suspension leaves the outlet aperture of the supply capillary, is adjustable.

This object is attained, according to the invention, in that the first chamber is closed with respect to the ambient atmospheric pressure and in that the electrolyte is delivered through a supply line from an antechamber whose height is adjustable. The level of the particle-free electrolyte with respect to the antechamber can be set independently of the height adjustment of the antechamber itself so that the height adjustment of the antechamber determines the pressure prevailing in the first chamber.

The use of a closed container for the first chamber makes it possible to adjust the static pressure therein independently of the external atmospheric pressure, namely by the height adjustment of the antechamber connected to it. However, this process makes it possible at the same time to arbitrarily adjust the excess pressure required for the outflow of the particle suspension from the supply capillary as measured with respect to the static pressure in the first chamber and this is done also by a height adjustment of the antechamber. Fluid in the supply capillary itself is subjected to normal atmospheric pressure. The excess pressure of the particle suspension with respect to the electrolyte contained in the first measuring chamber which determines the outflow velocity of the particle suspension from the supply capillary tube is the result of reducing the pressure of the first measuring chamber with respect to atmospheric pressure. This reduction can be arbitrarily set by adjustment of the height of the antechamber.

The invention also includes other advantageous further embodiments; among these are: the manner of adjusting the level of the electrolyte in the antechamber; the galvanic separation of the measuring chamber from the supply line of the electrolyte; the disposition of the measuring aperture so as to prevent the deposition of air bubbles in its vicinity; flushing the regions in front of and behind the measuring aperture; the capability of switching from normal operation to flushing; the embodiment of individual parts, such as the electrodes and the suspension container, as plug-in parts which are easy to handle and easy to clean; the generation of electrical signals by means of photoelectric cells related to the condition of the container holding the particle suspension and used for the control of the data evaluation process.

The invention will be better understood as well as further objects and advantages become more apparent from the ensuing detailed specificationof two exemplary embodiments taken in conjunction with the drawing.

BRIEF DESCRIPTION OF TH DRAWING

DESCRIPTION OF THE PREFERRED EMBODIMENTS

Figure 1:
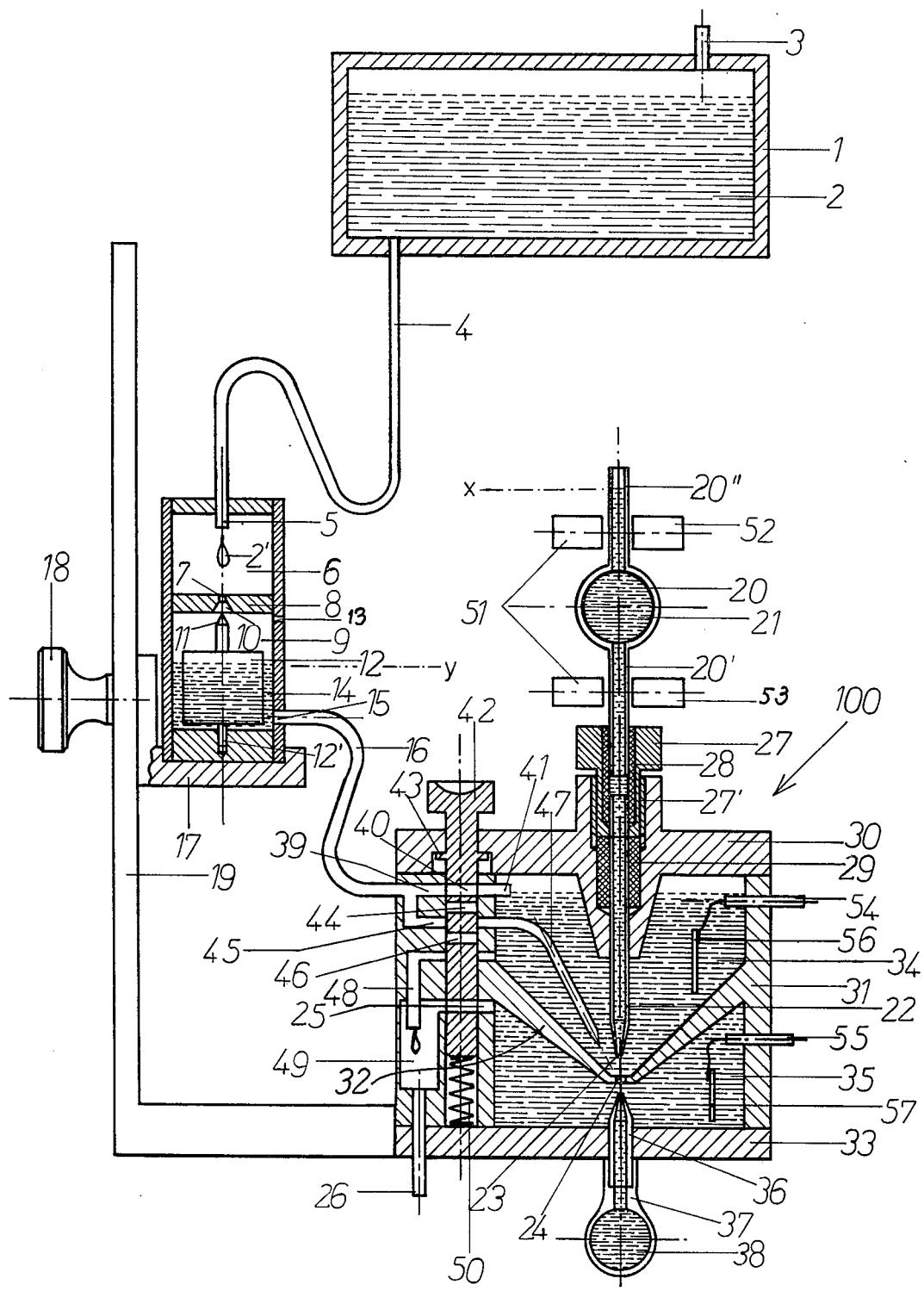
FIG. 1 is a cross section through a first exemplary embodiment of the invention.

The exemplary embodiment depicted in FIG. 1 includes a storage container 1 which contains particle-free electrolyte 2 and is vented through a venting aperture 3. The storage container 1 is connected by a flexible line 4 to a drip nozzle 5 from which the particle-free electrolyte emerges in the form of drops 2'. The dropwise supply of particle-free electrolyte to subsequent elements of the apparatus accomplishes a galvanic separation of the electrolyte 2, contained in the storage container 1, from the electrolyte contained in the further members of the apparatus. This separation effectively prevents an electrical interaction of the system to be described below with any electrical properties (capacities and the like) of the storage container 1 or the line 4. The drip chamber 6 is closed below by a separating wall 8 which includes an aperture 7. The electrolyte flows through the aperture into the antechamber 9, embodied as a float chamber, where it accumulates. Floating within the antechamber 9 on a guide mechanism 12' is a float 12 provided with a conical valve tip 11 which engages the matching valve seat 10 located at the bottom of the aperture 7. Thus, as soon as the electrolyte 14 within the flow chamber 9 has raised the float 12 so that the aperture 7 is closed by the valve tip 11, the flow of electrolyte is stoppwed. The valve composed of the valve tip 11 and the valve seat 10 therefore regulates the level of the particle-free electrolyte 14 within the antechamber 9 to a particular, constant value which is independent of external influences, especially of the height at which the antechamber 9 is located (see also below). The antechamber 9 is vented through a venting aperture 13.

The drip chamber 6 and the antechamber 9 are affixed to a support plate 17 which glides vertically along a guide rail 19 and whose height thereon may be adjusted by means of the set screw 18. The antechamber 9 is provided with an outlet 15 which is connected to the actual measuring chamber 100 (main chamber) by a flexible line 16.

The measuring chamber 100 is composed of a housing 31, a top cover 30, and a bottom cover 33. A separating wall 32 divides the main measuring chamber 100 into an upper chamber 34 and a lower chamber 35. As may be seen in FIG. 1, the separating wall 32 is not horizontal, but is downwardly conical so that the upper chamber 34 as well as the lower chamber 35 are somewhat funnel-shaped. This shape of the separating wall 32 is important in this exemplary embodiment especially as it determines the form of the lower chamber 35 (see further below). At its lowest point, the separating wall 32 has a measuring aperture 24 through which fluid contained in the upper chamber 34 may flow into the lower chamber 35. A first electrode 56 is located in the upper chamber 34 and a second electrode 57 is located in the lower chamber 35. The electrode contacts 54 and 55 permit electrical current to flow through the measuring chamber.

Particle-free electrolyte flows from the line 16 through the inlet nipple 41 into the upper chamber 34. From the lower chamber 35, the electrolyte, which is then no longer particle-free, (see below) flows through an outlet drip chamber 49 and is aspirated through a suction connection 26 leading to a source of reduced pressure (not shown). The supply of particle suspension into the chamber 34 takes place through a supply capillary tube 22 whose elongated, thin-walled and narrowing outlet tip 23 is disposed at a variable, i. e. adjustable distance above the measuring aperture 24. The supply capillary 22 is plugged into a central bore within the cover 30 and is held there by means of a clamping and sealing element 29 in which the supply capillary may slide to vary its relative height. A stuffing box 27' within the cover 30 holds a bushing 27 through the central bore of which a second clamping and sealing element 28 is inserted. The supply capillary 22 is centrally positioned thereby and extends downwardly into the lower region of the second clamping and sealing element 28. Extending into the upper portion of the clamping and sealing element 28 is the lower insertion stud 20' of a container 20 which is filled with particle suspension 21 up to a level within its upper filling stud 20''. Both the insertion stud 20' as well as the filling stud 20'' have a round cross-section and, when a fluid column is present in them, it acts as a collecting lens, i. e. it focusses the light passing through it. If no fluid is present in the insertion stud 20' or in the filling stud 20'', then the ligh passing through it is focussed substantially less due to the very different indices of refraction of glass and air. This fact is used to control the particle counting process with the aid of two light sources 51, a first photocell 52 and a second photocell 53 from which signals are obtained for controlling of the counting process. In particular, when the meniscus of the particle suspension falls to the level at which the light source 51 and the first photosensitive cell 52 are located, the absence of focussing produces a signal which can be used to begin the counting process. When the meniscus of the fluid falls to the level of the second photocell 53, a further signal is obtained which may be used to terminate the counting process. The volume of the container 20 lying between these two control levels can be calibrated so that certain types of electronic evaluation, for example the determination of the number of particles per volume of particle suspension 21 can be performed in this way. It should be emphasized at this point that the container 20 may simply be plugged in; it can be prepared at a remote location where the particle suspension (for example blood) is obtained and then can be placed onto the measuring chamber 100 without difficulty by plugging it into the clamping and sealing element 28 so that the measuring or data collection process can begin without further preparation. The two openings of the container 20, i.e. those of its insertion stud 20' and of the filling stud 20'' are so small that surface tension prevents the efflux of the particle suspension except when the pressure is in excess of that of the surroundings or when the tip is dipped into the fluid. Furthermore, the evaluation of several suspensions in several different containers 20 can occur sequentially and in a simple manner.

The actual measuring process proceeds in known manner: fluid (electrolyte and particle suspension) is aspirated from the chamber 35. This results in a pressure difference between the chamber 34 and the chamber 35 as a consequence of which fluid flows through the measuring aperture 24, the stream narrowing in the region ahead of the measuring aperture 24. Due to the fact that the pressure of the particle suspension 21 in the supply capillary 22 is higher than the pressure of the particle-free electrolyte in chamber 34, the particle suspension emerges from the outlet tip 23 of the supply capillary 22 and enters the concentrating flow of the particle-free electrolyte ahead of the measuring aperture 24. In this way, the thread of particulate stream emerging from the supply tip is narrowed and considerably concentrated. When a particle passes through the measuring aperture 24, the electrical resistance between the electrodes 56 and 57 is changed. This property may be used to derive a pulse which contains information related to the volume and/or other characteristics of the particle and which may also be used for counting the particles, i. e. a signal which, expressed in general terms, is evaluated in appropriate counting and/or classifying instruments.

An important characteristic of the present invention is that the outflow velocity of the particle suspension from the outlet tip 23 of the supply capillary 22 can be adjusted by regulating the excess pressure in the supply capillary 22 with respect to the static pressure prevailing in the chamber 34. This is done, as described above, in that the chamber 34 is closed so that the pressure within it depends on the height of the level y of the particle-free electrolyte 14 within the antechamber 9. This height, in turn, is determined exclusively by the height at which the support plate 17 is positioned and is adjustable by sliding this plate up or down on the guide rail 19. By placing the antechamber 9 so far down that the meniscus y of the particle-free electrolyte 14 lies below the upper surface of the electrolyte within chamber 34, the pressure therein can be made, in particular, negative with respect to the external atmospheric pressure. Nevertheless, the electrolyte does not flow from chamber 34 into the antechamber 9 but always flows in the opposite direction. This is due to the fact that the absolute pressure within the chamber 25 is always much lower than that in the chamber 34 and hence the liquid always flows from chamber 34 into chamber 35.

The pressure of the particle suspension in the supply capillary 22 depends on the height of the level $x$; and this means that the pressure difference $$D = f(y - x)$$

which determines the efflux of particle suspension 21 from the outer tip 23 can be adjusted by setting the level difference $y - x$ and hence by setting the level $y$.

The decisive adjustment of the excess pressure of the particle suspension within the supply capillary, which determines the outflow pressure and hence the outflow velocity (measuring rate) thus does not depend exclusively on the height of the column of the particle suspension 21 within the supply capillary 22, but depends primarily on the reduction of pressure within the closed-off volume 34 and this pressure is obtained by adjusting the height of the antechamber 9 on the guide rail 19. Thus, when using such measuring chambers, it is possible not merely to measure this parameter very exactly, but also to adjust it very exactly and to change it, even during the measurement, in simple manner.

In this way, one can also control the efflux of particle suspension from the outlet tip 23 of the supply capillary. For if the antechamber 9 is placed at such a height that the static pressure it produces in chamber 34 is not at least lower than the pressure of the particle suspension in the supply capillary 22 by a particular threshold value, then the supply of particle suspension is "shut off". Lowering the antechamber 9 can restart the flow of particle suspension into the chamber ahead of the measuring aperture and can also accelerate it. The "threshold value" is determined by the flow resistances occurring within the supply capillary 22 when it is dipped into the electrolyte.

The static pressure referred to is the pressure within chamber 34 which is produced in the above described sense by adjusting the height of the antechamber 9 (without considering the flow occurring anywhere in the system or the pressure changes or reductions which would be calculated by Bernoulli's equation but which play no role for the dimensions used in this apparatus). The gage pressure in the chamber 35 is approximately - 4m $H_2O$ with respect to the external atmospheric pressure whereas in the chamber 34 it is equal to - 6cm $H_2O$ with respect to the external atmospheric pressure. The pressure within the supply capillary 22 which is connected to the atmosphere is therefore at a static positive value of 1 to 6cm $H_2O$ with respect to the chamber 34. Thus, the pressure reduction within the chamber 35 to 100 times as great as that in the chamber 34 and, therefore, the influence of the different pressures in the chambers 34 and 35 may be neglected as it affects the flow through the measuring aperture.

This "dry" regulation of the particle stream density makes possible an arbitrary stopping and restarting of a measurement as well as changing the number of particles per unit time which are measured. In the same way, it is possible to effect a reversal of the streaming direction so as to assist in flushing the supply capillary 22.

The disposition of the outlet opening 25 at the uppermost point of the separating wall 32 which extends conically downward toward the measuring aperture 24 serves to vent the lower chamber 35. When air bubbles are produced, they are sucked out at this highest location. The shown embodiment of the separating wall 32 and the disposition of the measuring aperture 24 therein at a point which is lower than the aperture 25 therefore prevents what normally occurs with a horizontal separating wall, namely that air bubbles adhere to the separating wall in or about the region of the measuring aperture 24 and lead to a falsification of the results of the measurements.

A flushing capillary 47 is disposed in the vicinity of the measuring aperture 24 and of the outlet tip 23 of the supply capillary 22 for the purpose of flushing a region ahead of the measuring aperture 24 free of particulate material and of air bubbles which may collect there. This flushing is obtained by downward pressure on a control piston 42 which is normally urged by a spring 50 engaging a collar 43 to move against the stop within the cover 30. When the control piston is pushed down, the passage 40 within it is so displaced that the communication of the inlet opening 39 with the inlet stud 41 is interrupted while the passage 44 is so displaced that it creates a communication of the inlet opening 45, also connected to the line 16, with the flushing capillary 47. If the flow chamber 9 is placed sufficiently high up, then a stream of electrolyte emerges frm the tip of the flushing capillary 47 and loosens and raises up any particles which may have been deposited in front of the measuring aperture 24 because they were too large to pass through it. These particles flow out through an outlet 48 which communicates with the chamber 34 through a passage 46 in the control piston when it is pressed down. Their removal takes place, in the manner shown in FIG. 1, through the drip chamber 49.

A flushing nozzle 36 is located in the chamber 35 at a small distance in front of the measuring aperture 24 for flushing the lower side of the measuring aperture 24 and also for loosening and raising up particles which may have been deposited there, but it also serves for the removal of very small air bubbles which may still adhere to surfaces in spite of the venting provided. This flushing nozzle 36 communicates with a compressible container 37 which contains a supply 38 of liquid electrolyte which streams from below in the direction of the measuring aperture 24 when the container 37 is squeezed, producing the desired cleaning effect.

Figure 2:
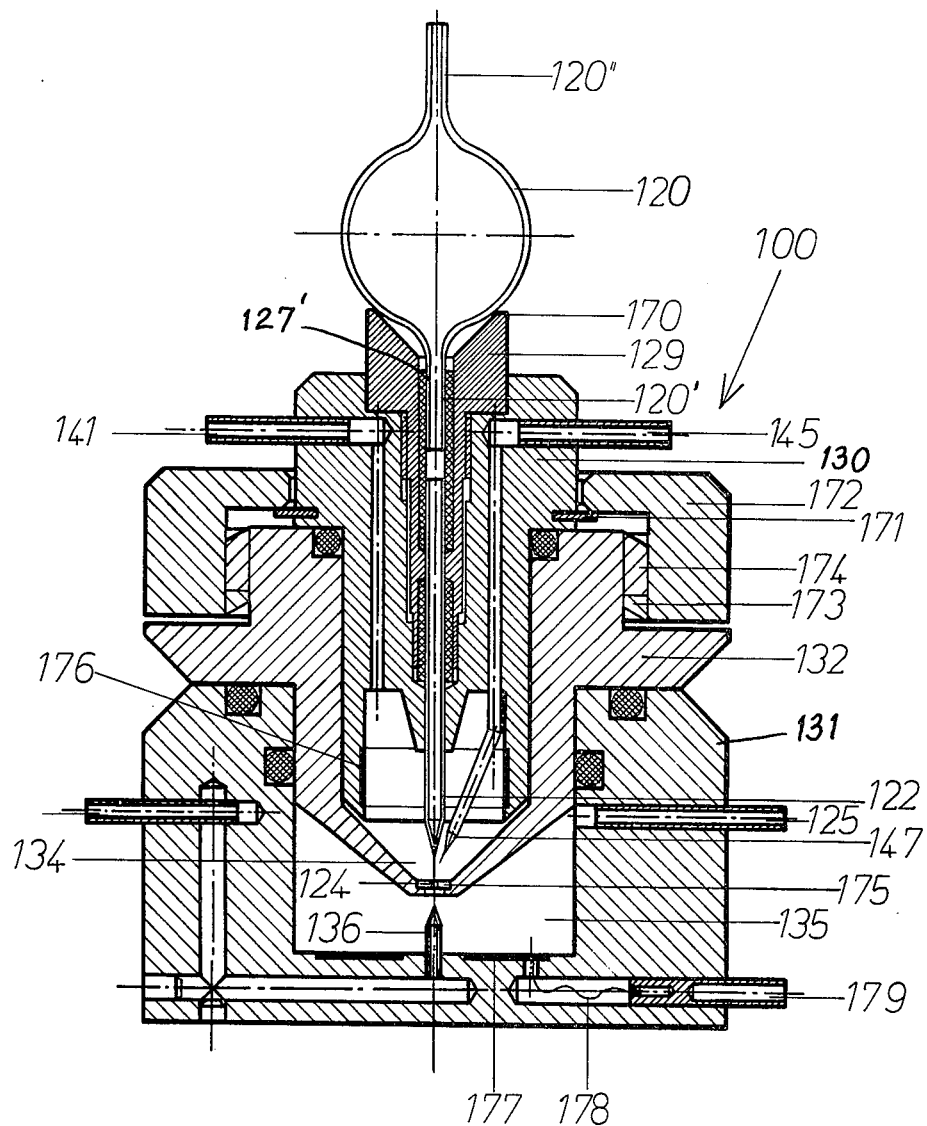
FIG. 2 is a cross section through a second exemplary embodiment of the invention.

FIG. 2 shows a second exemplary embodiment of the measuring chamber 100 in somewhat more detail. It shows in particular especially practical realizations and further developments residing in the simple plug-in connection and easy handling of the parts, further simplifying the operation and especially the cleaning and the exchange of several parts.

The measuring chamber 100 is formed by a lower dome-shaped housing member 131 holding an insert member 132 that has a downwardly conical surface. Inserted in the latter is an upper member 130 designed in the manner of a stuffing box whose lower end has a hollow cylindrical void and whose lower circumferential edge is beveled. The upper member 130 holds a clamping and sealing member 129 whose height is adjustable in a stuffing box 127'. The supply capillary 122 is inserted into the bore of the clamping and sealing member 129 and extends down through it and through the upper member 130.

The clamping and sealing member 129 is enlarged at its upper end in such a way that it forms an upwardly enlarging sealing lip 170 on which rests a container 120 for the particle suspension and which limits the height to which the container may be inserted into the clamping and sealing member 129.

The upper member 130 has a shoulder 171 on which rests a collar 172 with extensions 173 which engage extensions 174 located on the insert member 132 in the manner of a bayonet closure.

The upper member 130 also includes a supply line 141 for supplying particle-free electrolyte from a line which corresponds to the line 16 in FIG. 1.

The upper member 130 also includes a flushing capillary 147 which can be supplied with rinsing fluid through a channel 145.

The insert member 132 also includes a plate insert 175 in which the actual measuring aperture 124 is located.

One electrode 176 is located in the insert member 130 on the wall of the lower cylindrical void as a plate or an evaporated layer. This embodiment of the upper member 130 creates a capture space for bubbles which are formed in chamber 134. These air bubbles collect at the top and are carried out through the connecting line 141 when the apparatus is flushed. (See below.) The other electrode is formed by a plate 177 attached to the bottom of the housing member 131. The electrical supply line for the electrode 176 is not shown in FIG. 2. It is incorporated in the corresponding apparatus elements and provided with external connectors.

The bottom of the insert member 132 divides the interior space of the housing member 131 into a lower chamber 135 and an upper chamber 134. These chambers communicate via the measuring aperture 124. Particle-free electrolyte is supplied through the inlet line 141 and is removed by suction out of the chamber 131 through the suction channel 125. The measuring aperture 124 is flushed from below through a flushing channel 136. As may be seen, seals are provided in various places to seal individual parts with respect to one another.

The advantage of the embodiment depicted in FIG. 2 lies in the simple exchangeability of individual parts. Especially noted in this connection should be the simple manner of inserting the container 120 and, as has already been mentioned in connection with FIG. 1, this may serve to make sequential measurements with a particular measuring chamber where a sequence of measurements can be prepared by filling several containers with particle suspension (for example blood) in advance.

The disposition according to FIG. 2 can also include means for generating signals for starting or stopping the evaluation or counting process and these means may be photoelectric cells provided at the level of the inlet stud 120″ or of the insertion stud 120′.

Of considerable importance is the plug-in capability of the insertion member 132 as well as of the upper member 130 contained therein and that the lower part of the upper member 130 carries an electrode 176 which is annular in the exemplary embodiment of FIG. 2 but which can be of different construction. A control piston of the type provided in the exemplary embodiment of FIG. 1 is not an integral part of the measuring chamber 100 in the present exemplary embodiment according to FIG. 2. A switchover to a flushing process must be effected by externally provided valves: in a first switching position thereof (normal operation), particle-free electrolyte is delivered through the inlet line 141, whereas the channel 145, which is connected to the flushing capillary 147, is pressure-free. In a second control position (flushing) the supply of particle-free electrolyte is switched over from the inlet line 141 to the channel 145 and, at the same time, the source of reduced pressure, which is normally connected to the suction channel 125 is switched over to the inlet line 141. Thus, the flushing process, as has already been mentioned, serves for loosening and removal of particles which have been disposed in front of the measuring aperture 124 because they were too large for passage therethrough.

We claim:

1. In an apparatus for the measurement of properties of particles held in suspension including: a housing defining therein a main measuring chamber separated into a first and a second chamber; a separating wall separating both chambers and having a measuring aperture formed therein connecting the first and second chamber, wherein the first chamber is supplied with particle-free electrolyte; means connected to the second chamber for maintaining the pressure in the second chamber below the pressure in the first chamber causing thereby the electrolyte to flow from the first chamber through the measuring aperture into the second chamber; a first electrode mounted with the first chamber; a second electrode mounted with the second chamber; and a supply capillary tube subject to the surrounding atmospheric pressure for receiving the suspension and having an outlet, said supply capillary tube being mounted to extend with its outlet into the first chamber such that to allow the suspension to enter into the first chamber and be carried through the measuring aperture with the electrolyte, when the pressure in the supply capillary tube exceeds the pressure in the first chamber around the outlet, the improvement comprising:
- a. said housing constructed to pressure isolate the first chamber from the surrounding atmosphere; and
- b. a source of variable pressure connected to the first chamber for providing within said first chamber a variable pressure less than atmospheric pressure and above the pressure in the second chamber to effect the flow of particles containing suspension from the supply capillary tube into the first measuring chamber.

2. An improved apparatus as defined in claim 1, wherein the separating wall has substantially the shape of a cone whose apex points in the direction of said second chamber, said cone being further provided with an outlet aperture near the base of the cone; whereby said outlet aperture lies substantially higher than the measuring aperture when the apparatus is in its normal operating position.

3. An improved apparatus as defined in claim 1, wherein the improvement further comprises:
- g. flushing means mounted to the housing and extending into the second chamber; whereby fluid may be moved in and around the measuring aperture.

4. An improved apparatus as defined in claim 3, wherein said flushing means includes a compressible fluid container; whereby fluid may be moved out of said flushing means by compression of said compressible container.

5. An improved apparatus as defined in claim 1, wherein the improvement further comprises:
- h. a capillary flushing tube mounted to the housing and extending into the first chamber; whereby fluid may be moved in and around said measuring aperture.

6. An improved apparatus as defined in claim 5, wherein the improvement further comprises:
- i. a source of reduced pressure;
- j. control means disposed adjacent to said main measuring chamber and capable of two control positions: a first control position, in which communication is established between the antechamber and the first chamber and also between the exterior of the apparatus and the second chamber; and a second control position, in which communication between the antechamber and the first chamber is interrupted and a communication is established between the antechamber and said capillary flushing tube, and between said source of reduced pressure and the second chamber, whereas the communication of the second chamber with the exterior of the apparatus is interrupted.

7. An improved apparatus as defined in claim 1, wherein the improvement further comprises:
- k. a clamping and sealing element, mounted in the wall of the housing at the first chamber; whereby said supply capillary tube is inserted in a bore within said clamping and sealing element so as to extend into the first chamber.

8. An improved apparatus as defined in claim 1, wherein the improvement further comprises:
- l. a supply container, for holding a supply of particle suspension, said supply container being provided with an inlet stud and an insertion stud, respectively at opposite ends thereof, and of circular cross-section.

9. An improved apparatus as defined in claim 8, wherein the cross-section of said inlet stud and of said insertion stud is sufficiently small that the particle suspension contained in said supply container is retained therein unless it is placed in contact with fluid external thereto.

10. An improved apparatus as defined in claim 8, wherein the improvement further comprises:
- m. a bushing, mounted in the wall of the housing at the first chamber; and
- n. a second clamping and sealing element disposed coaxially in the bore of said bushing, whereby said container for particle suspension may be inserted into said second clamping and sealing element, thereby permitting flow of particle suspension from said container to said supply capillary tube.

11. An improved apparatus as defined in claim 9, wherein the improvement further comprises:
- o. photoelectric means, including a light source and a photosensitive cell, disposed at said inlet stud and at said insertion stud in such a manner that a signal is generated by said photoelectric means to indicate the presence of particle suspension in the respective stud.

12. An improved apparatus as defined in claim 11, wherein the signals generated by the photosensitive cells serve to initiate and terminate the analysis of the signals generated by the first and second electrodes.

13. An improved apparatus as defined in claim 1, wherein the improvement further comprises:
- p. a removable insert formed as one portion of the housing, said insert defining a bore and having a lower wall which forms the separating wall containing the measuring aperture, said insert forming with the remainder of the housing, said first and second chambers;
- q. an upper member, centrally inserted into said removable insert and provided with a central bore, the lower part of which is capable of holding said supply capillary tube; and
- r. a clamping and sealing member, removably inserted into said upper member, provided with a central bore and also provided with a surface which limits the depth of insertion of a container of particle suspension into said central bore.

14. An improved apparatus as defined in claim 13, wherein said first electrode is mounted on an interior surface of said upper member.

15. An improved apparatus as defined in claim 14, wherein said first electrode is disposed in the central bore within said upper member, and has the form of an annulus concentric with said supply capillary tube.

16. An improved apparatus as defined in claim 15, wherein the improvement further comprises:
- s. a locking ring, disposed to cooperate with said removable insert in the manner of a bayonet closure so as to clamp said upper member to said removable insert.

17. An improved apparatus as defined in claim 16, wherein the improvement further comprises:
- t. a flushing capillary tube, wherein said upper member contains a first internal channel for supply or removal of electrolyte from the first chamber and a second internal channel for supplying flushing fluid to said flushing capillary tube.

18. An improved apparatus as defined in claim 17, wherein the improvement further comprises:
   u. a supply container, for holding particle suspension, removably and sealingly disposed in said central bore of said removable insert.

19. An improved apparatus as defined in claim 1, wherein the means for providing a pressure less than atmospheric pressure within the first chamber comprises:
   c. an antechamber, which is filled with particle-free electrolyte, said particle-free electrolyte being subject to atmospheric pressure;
   d. control means for keeping the level of electrolyte within the antechamber at a position, predetermined and constant with respect to the antechamber, irrespective of the height of the antechamber with respect to the first chamber;
   e. connecting means for supplying electrolyte from the antechamber to the first chamber; and
   f. means for varying the height of the antechamber with respect to the first chamber.

20. An improved apparatus as defined in claim 19, wherein said control means are within said antechamber, and include:
   i. valve means; and
   ii. float means,
whereby said float means closes said valve means when the level of the electrolyte has reached a predetermined value, thereby stopping the flow of electrolyte to the first chamber.

21. An improved apparatus as defined in claim 19, wherein the improvement further comprises:
   f. a drip chamber, disposed in said antechamber, for providing electrical un-coupling of the electrolyte in said antechamber from its source of supply.

22. An improved apparatus as defined in claim 19, wherein said antechamber is provided with a vent opening, creating a communication to the exterior thereof.

* * * * *